United States Patent
Thorne, Jr. et al.

(10) Patent No.: US 9,005,170 B2
(45) Date of Patent: Apr. 14, 2015

(54) PROTECTION AGAINST SPILL AND SYRINGE RELATED CONTAMINATION

(71) Applicants: Gale H. Thorne, Jr., Bountiful, UT (US); Kendall P. Thorne, Layton, UT (US)

(72) Inventors: Gale H. Thorne, Jr., Bountiful, UT (US); Kendall P. Thorne, Layton, UT (US)

(*) Notice: Subject to any disclaimer, the term of this patent is extended or adjusted under 35 U.S.C. 154(b) by 0 days.

(21) Appl. No.: 13/987,710

(22) Filed: Aug. 24, 2013

(65) Prior Publication Data

US 2014/0107612 A1 Apr. 17, 2014

Related U.S. Application Data

(63) Continuation-in-part of application No. 13/066,565, filed on Apr. 18, 2011, now abandoned.

(60) Provisional application No. 61/699,963, filed on Sep. 12, 2012.

(51) Int. Cl.
*A61M 5/32* (2006.01)
*A61M 31/00* (2006.01)
*A61M 5/00* (2006.01)

(52) U.S. Cl.
CPC .................................. *A61M 5/001* (2013.01)

(58) Field of Classification Search
USPC ........................................................ 604/199
See application file for complete search history.

(56) References Cited

U.S. PATENT DOCUMENTS

| 5,976,112 | A | 11/1999 | Lyza, Jr. |
| 7,766,304 | B2 * | 8/2010 | Phillips ..................... 251/149.6 |
| 7,803,140 | B2 * | 9/2010 | Fangrow, Jr. ................. 604/256 |
| 2007/0106226 | A1 | 5/2007 | Croll et al. |

* cited by examiner

*Primary Examiner* — Jason Flick
(74) *Attorney, Agent, or Firm* — Gale H. Thorne

(57) ABSTRACT

Methods and apparatus for employing an adhesive strap about a medical connection for improving connection integrity for greater safety and reliability and a cross contamination barrier for medical syringes is disclosed. Also, a shielding tube for a medical syringe which acts as a barrier against cross contamination across a syringe plunger is disclosed. The tube comprises a pattern of raised ribs inside to protect against potentially tube tearing edges of an associated plunger rod assembly and to provide a skid resistant surface when disposed about flanges of the syringe.

7 Claims, 4 Drawing Sheets

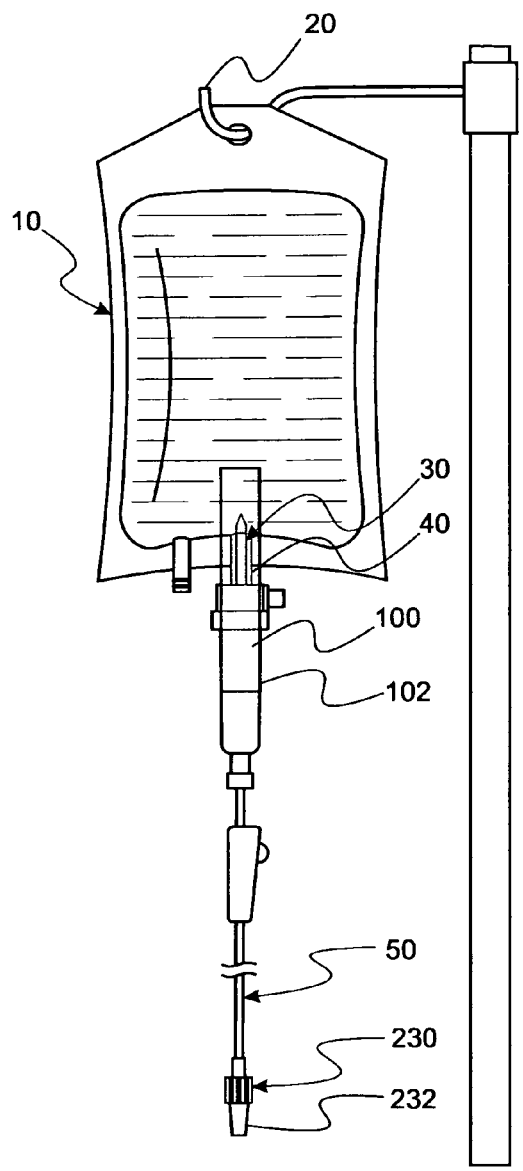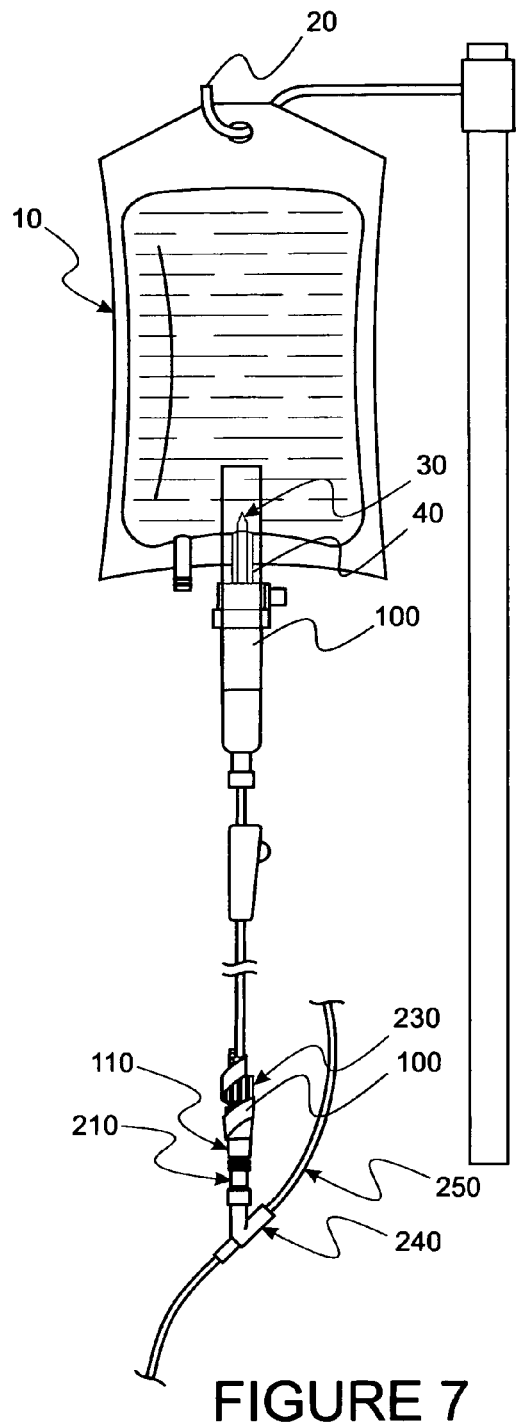
FIGURE 1
FIGURE 7

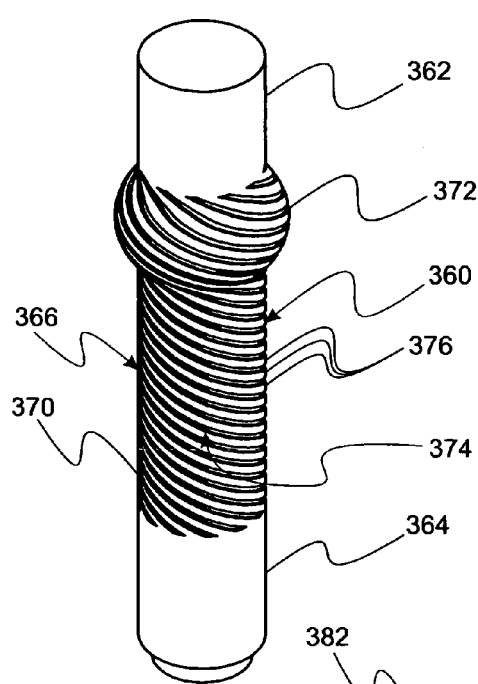
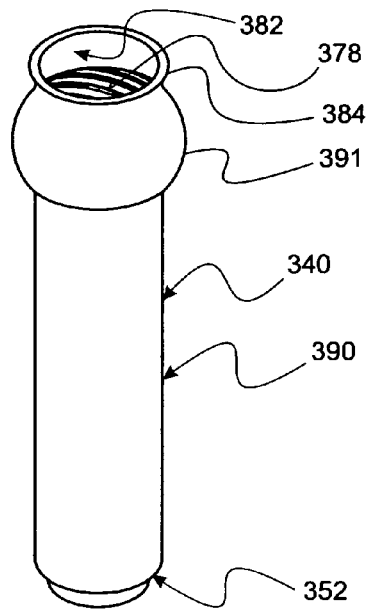
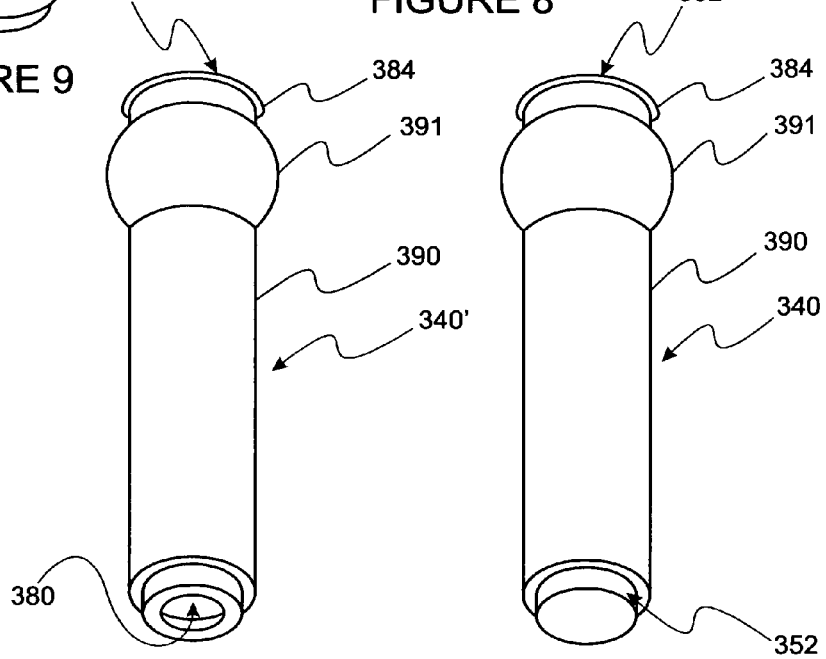
FIGURE 9
FIGURE 8
FIGURE 11
FIGURE 10

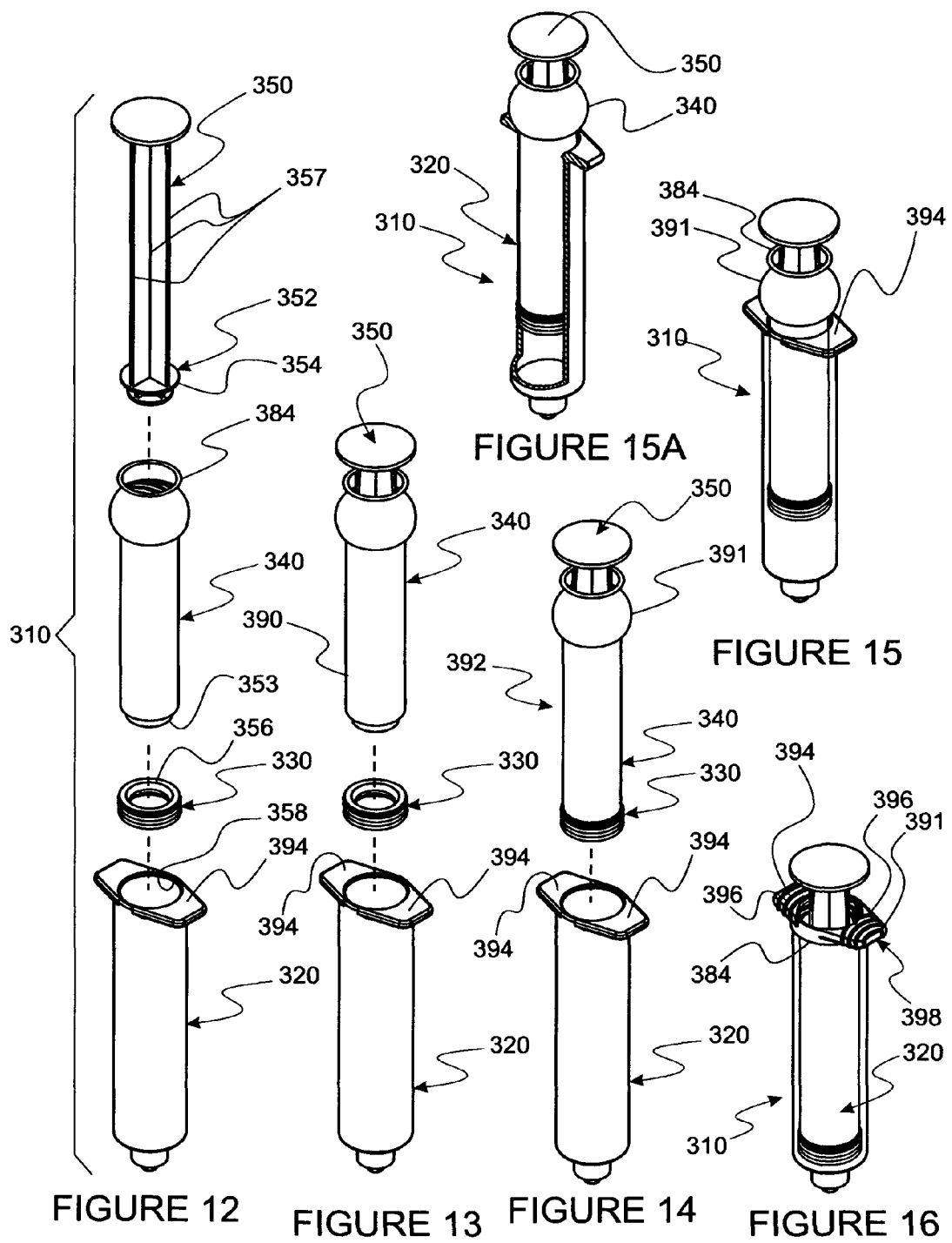

PROTECTION AGAINST SPILL AND SYRINGE RELATED CONTAMINATION

CONTINUATION IN PART

This Patent Application is a CONTINUATION-IN-PART of a Provisional U.S. Patent Application 61/699,963 filed by Gale H. Thorne, et al. (Thorne 963). Sep. 12, 2012 and titled PROTECTION AGAINST SPILL AND SYRINGE RELATED CONTAMINATION which is a CONTINUATION-IN-PART of U.S. patent application Ser. No. 13/066,565 filed by Gale H. Thorne, et al. Apr. 18, 2011, and titled MEDICAL SYRINGE PRIME AND CROSS CONTAMINATION FREE DEVICES which are made part hereof by reference.

FIELD OF INVENTION

This invention relates to medical connections and syringe plunger interfaces whereat inadvertent spills and cross contamination can occur.

BACKGROUND AND RELATED ART

When dealing with syringes, generally two modes of concern, i.e. spills and cross contamination should be considered. The first, being of greatest concern in oncology and other hazardous drug handling, deals with spills which may occur at a luer connecting interface, e.g. at the connecting end of a syringe. As most often provided, each syringe has an open orifice within a luer-lock interface. When that interface is inadvertently opened, resulting drug spills are often considered very dangerous.

In broader scope, methods related to the instant invention comprise processes for using connectors which are affixed via a friction fit. Examples of such connectors are bag spikes and luer-lock fittings. The desirability for increased safety for such connectors has been well established by spikes which have been inadvertently pulled from a bag and by syringe affixed luer fittings which have been twisted free when attempting to disconnect an associated fitting connected in tandem. It is important to note that employing a needleless connector and a dripless needleless connector adapter requires two connectors be placed in tandem forming a common flow path there through. Dangers associated with disengaging the wrong connector are well known in medical art, especially when handling oncology or other hazardous drugs.

Noting that each syringe to connector adapter and connector adapter to needleless connector interconnection is disengaged by rotation in the same direction, it becomes evident that there is a need for some differentiating feature to assure the wrong connection is not disengaged. As it is critical that only the needleless connector/connector adapter interface be disengaged when breaking the flow path, it is commonly taught, through in-servicing, to grasp the connector adapter when performing a disengagement rotation to assure the syringe/connector adapter interconnection remains secure. However, experience has shown that inadvertent rotation of an associated syringe rather than grasping the connector adapter can occur and when stiction (force required to overcome static friction and initiate motion) of the syringe/connector adapter interface is less than stiction of the needleless connector/connector adapter interface. In such a case, the syringe can be resultingly disengaged from the connector adapter providing opportunity for a spill.

An example of a special connector designed for improved securement is the Spinning Spiros® available from ICU Medical, San Diego, Calif. Once secured to a site, the Spinning Spiros is designed to physically detach connection between parts which are disposed to be radially displaced to free the Spiros.

The second mode of concern is residue which is distributed across the inner wall of a syringe barrel by bidirectional displacement of an associated plunger. Of course, when a plunger is displaced to dispense fluid from the syringe, any material not wiped from the inner wall of the barrel becomes residue which is available to the open proximal end of the syringe. Similarly, any contamination on the barrel wall proximally disposed relative to the plunger of the syringe which is not wiped when the plunger is proximally displaced is left to contaminate fluid within the barrel which is distally disposed to the plunger.

An example of a special device which is commercially available for addressing this problem is EquaShield® made and distributed by EquaShield Medical, Ltd. The EquaShield is designed to replace fluid drawn from a vial or other liquid source with fluid originally disposed in the proximal end of a closed syringe barrel to obviate cross contamination across a plunger.

Other cross contamination barriers for medical syringes are known in the medical art. Examples of art disclosing such barriers are found in U.S. Pat. No. 5,976,112 (now abandoned) which was filed by Henry Walker Lyza, Jr (Lyza) and allowed. Nov. 2, 1999 and titled INJECTOR SYRINGE. In addition, a U.S. Patent Application 2007/0106226 filed by Perry W. Croll, et al. (Croll), and titled SYRINGE WITH INTERNAL SLEEVE filed Nov. 9, 2005, and the U.S. Patent Application cited as Thorne 963, supra, provide other related art.

Each of the examples cited supra disclose a tube of substantially constant diameter and thickness between a distal end portion and a rolled proximal end part. As well, all disclose that material used in such tubes is sufficiently elastic to be wrapped around syringe flanges such that the rolled proximal end part can form a barrier about the barrel of the syringe.

In practice, it has been found that wear during use and storage, changes in material due to aging and sterilization procedures and stress associated with stretching such material about flanges of an associated syringe can result in material failure in tubes of substantially constant diameter and thickness resultingly uncovering parts of the associated syringe to undesirable external exposure. In particular, it has also been found that shearing along edges of plunger rods (and more particularly along plunger rod edges with parting lines) associated with displacement of syringe plungers at the commonly provided retention ring of a conventional syringe is a source of material tearing and resulting malfunction.

Such external exposure can have serious consequences because exposure to sources external to the syringe can contaminate the inside of a syringe barrel with material which may be communicated into a syringe delivery chamber distal to a syringe plunger. In like manner, if material in the distal chamber of a syringe is hazardous and is communicated into a portion of the barrel of the syringe proximal to the syringe plunger, such can also lead to serious consequences. For these reasons, it is critical that robustness of the material assures that such failures do not occur.

Further, syringe flanges provide a digital interface which often involve gloved hands. As such that interface, as part of the instant invention, involves a portion of a cross contamination tube disposed about the flanges presenting a surface which is characteristic of material used in the tube. Care must be taken that such an interface is not too slick, not allergenic and preferably presents an improved (e.g. skid resistant) digital contact surface.

BRIEF SUMMARY AND OBJECTS OF THE INVENTION

Luer Fitting Securement

Generally, securement methods and apparatus for the instant invention employ an adhesive flexible strap which is disposed across or about interconnecting parts to provide a cinch for a medical connection. In all cases the strap must have sufficient tensile strength to withstand reasonable forces applied to disengage the connection. In like fashion, adhesive associated with the strap should adhere well enough to withstand similar reasonable sheer forces applied to the strap when affixed to an associated surface. It has been determined that plastic label material with extra strength adhesive serves these purposes well.

Methods for attaching an adhesive strap according to the present invention vary from application to application. As an example, strap attachment may be simply in the form of a linear connection between a bag and a spike extension across the spike/bag interface.

Another example is use of the strap to secure a connection between a male luer-lock fitting and a part comprising a female luer fitting, such as affixing a dripless connector to a male luer-lock connector (e.g. a medical syringe). In such a case, the strap is wound about a body part of the dripless connector (female luer-lock fitting) in a direction counter to direction of rotation which disconnects the fitting. A free part of such a strap is affixed to a body part of the associated device providing the female luer fitting (e.g. barrel of a syringe). In the case of affixing a strap to a syringe barrel, it has been determined that an angle of attachment is important for optimally securing the strap to the barrel. To communicate the angle, at least one line printed on the strap is preferably provided to coincide with a bottom barrel ridge of the associated syringe.

Generally, the strap is affixed to the associated dripless connector prior to a syringe engagement. When the syringe and dripless connector are tightly engaged, the strap is wound counter to disengagement rotation and affixed to the barrel of the syringe. In this manner, disengagement by rotation of the syringe is assured to only disengage the needleless connector/dripless connector interconnection.

Accordingly, it is a primary object to provide methods for applying an adhesive strap across or about a medical connection to provide a cinch against inadvertent disconnection.

It is a very important object to provide a method for securing a dripless connector female luer-lock fitting to a male luer-lock fitting which obviates inadvertent rotation and disengagement of an associated connection.

It is also an important object to provide a method for securing a bag spike to a bag.

Cross Contamination Barrier

In brief summary, this novel invention alleviates all of the known problems related to providing intra syringe barrel cross contamination tubes which are of robust design and of reduced susceptibility to material malfunction. As such, inventive processes disclosed herein provides a surprisingly improved cross contamination barrier.

Cross contamination barrier tubes made according to the present invention comprise a distally disposed portion which is formed and shaped to be captured and provide a seal where a plunger rod assembly is securely affixed to a syringe barrel plunger. The plunger being sized and shaped to wipe fluid from an inside syringe barrel wall while being displaced there along.

Continuously affixed to and proximally disposed from the distally disposed portion is an elongated portion which is preferably at least as long as plunger displacement distance within the syringe barrel. Disposed proximally from the elongated portion is a portion having an expanded girth whereby the expanded portion can be disposed about flanges of the syringe without undue material stress after being so disposed. Proximal from the expanded portion, the barrier tube comprises a rolled section (similar the mouth of a balloon) which circumscribes an open mouth, the mouth being sized to fit snugly about an associated syringe barrel to provide a treacherous path against cross communication of barrel associated contaminates.

Contemporarily, the tube is preferably made from nitrile rubber and preferably presents a smooth, solid and continuous exterior barrier surface from plunger to barrel exterior where the mouth of the tube engages the barrel. However, the interior surface of the elongated portion and expanded portion are formed with a pattern of raised ribs which have sufficient height, density and thickness to provide a safeguard against shearing edges of plunger rods and to provide a skid resistant surface about flanges of an associated syringe.

Accordingly, it is a primary object to provide a robust, reliable and effective cross contamination barrier tube for a medical syringe.

It is an important object to provide a tube which is robust and resistant to effects of shearing contact with an associated plunger rod.

It is also an important object to provide a cross contamination barrier tube a portion of which, being disposed about flanges of a syringe, presents a skid resistant surface at a digital interface.

It is yet another important object to provide a cross contamination barrier tube which has an expanded portion having a girth which permits enveloping flanges of a syringe without undue elastic stress.

The objects disclosed supra and features of the present inventions will be apparent from the detailed description taken with reference to accompanying drawings.

BRIEF DESCRIPTION OF THE DRAWINGS

FIG. 1 is front elevation of a hung bag wherein an inserted spike is secured from inadvertent disengagement by an adhesive strap applied to the bag on one end of the strap and to a portion of the bag spike on the other end of the strap.

FIG. 7 is front elevation of a hung bag, similar to FIG. 1, wherein an inserted spike is secured from inadvertent disengagement by an adhesive strap applied to the bag on one end of the strap and to a portion of the bag spike on the other end of the strap; however, a safety strap disposed across an interconnection between a luer fitting at the end of an IV secondary set tube and a dripless connector which is further connected in tandem to a needleless connector is also seen.

FIG. 8 is a perspective of a barrier tube made according to the present invention.

FIG. 9. Is a perspective of a mold or former for the barrier tube seen n FIG. 8.

FIG. 10 is a perspective of the barrier tube seen in FIG. 8, but tilted for a view of the distal or bottom portion of the tube.

FIG. 11 is a perspective of a barrier tube similar to the barrier tube seen in FIG. 10, but with a hole disposed in a distal portion of the tube to permit fluid flow there through.

FIG. 12 is an exploded view showing parts of a conventional syringe used with a barrier tube made according to the instant invention.

FIG. 13 is an exploded view, similar to the view seen in FIG. 12, but with a plunger rod inserted into a barrier tube.

FIG. 14 is an exploded view, similar to the view seen in FIG. 13, but with a plunger affixed to a barrier tube and inserted plunger rod.

FIG. 15 is an assembled perspective of a plunger rod inserted into barrier tube which is inserted into an associated plunger which is further inserted into a syringe barrel.

FIG. 15A is a cross section of the assembled perspective seen in FIG. 8.

FIG. 16 is a perspective of a fully assembled syringe and barrier tube with a portion of the barrier tube disposed about flanges of the syringe barrel.

DETAILED DESCRIPTION OF THE ILLUSTRATED EMBODIMENTS

Figure 2:
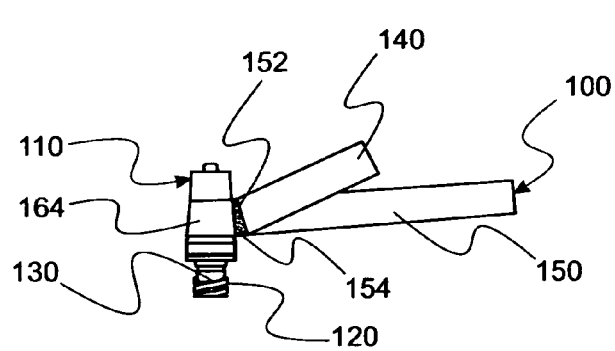
FIG. 2 is a frontal elevation of a dripless connector having a female luer-lock fitting and an adhesive strap wound about a portion of the body of the fitting, the winding being counter to direction of rotation associated with disconnecting the luer fitting from an associated male luer-lock fitting.
Figure 3:
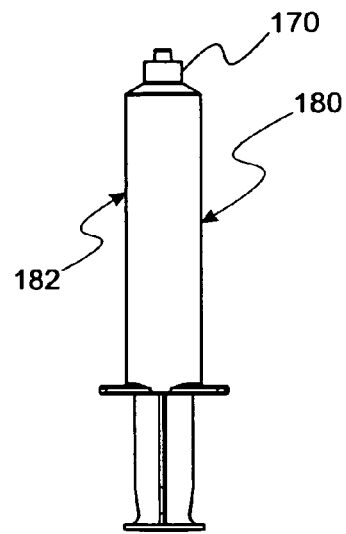
FIG. 3 is a frontal elevation of a conventional medical syringe having a male luer-lock fitting.

In this disclosure, the term proximal is used to indicate the segment of the device normally closest to the object of the sentence describing its position. The term distal refers to the other end. Reference is now made to the embodiments illustrated in FIGS. 1-16 wherein like numerals are used to designate like parts throughout. Primes of numbers are used to designate similar, but not identical, parts.

Safety Strap

Referencing FIGS. 1-7, a spiked bag 10 is seen hung from an elevated hook 20 in FIG. 1. A spike 30 is inserted through a bag port 40. Spike 30 is affixed as part of a secondary IV set 50. Such sets are currently commercially provided in many different configurations for delivery of fluids from a bag 10 to a patient.

To reduce likelihood of inadvertent disengagement of spike 30 from port 40 an adhesive strap 100 is adhesively affixed to bag 10 and a proximal portion 102 of set 50. So disposed, force required to disengage spike 30 from port 40 is measurably increased thereby decreasing likelihood of separation and associated spill.

Generally, strap 100 may be an adhesively backed inelastic material. Straps may be made from synthetic resinous material having sufficient tensile strength to withstand ordinary pull forces. As an example, and preferably, a strap 100 may be made using 1 mil thick polystyrene overlaid with a 2 mil thick layer of polyethylene and a permanent high tack (strong strength) adhesive. Also strap 100 is preferably transparent. Strap 100 and associated adhesive should withstand radiation and other forms of sterilization which may be applied to sterilize an associated connector.

Attention is now drawn to FIG. 2 where a dripless connector 110 is seen. Dripless connector 110 has a female luer-lock connection 120 having connecting threads 130 which are rotated in a first direction for engagement and an opposite direction for disengagement. Strap 100 has a portion 140 of a protective backing 150 peeled away from a surface 152 whereupon a layer of adhesive 154 is spread. Baring portion 140 permits a section 164 of strap 100 to be adhesively affixed about connector 110. So disposed, connector 110 may be affixed to a male luer-lock fitting (e.g. a male luer-lock fitting 170 which is part of a barrel 180 of a medical syringe 182, seen disconnected in FIG. 3). An exemplary size for strap 100 is ½ inch by 4 inches.

Figure 4:
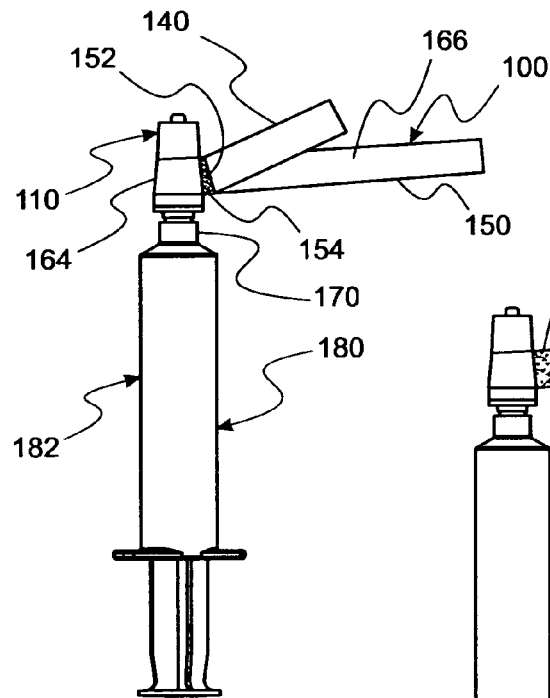
FIG. 4 is a frontal elevation of the dripless connector seen in FIG. 2 affixed via luer-lock connection to the syringe seen in FIG. 3.
Figures 5, 6:
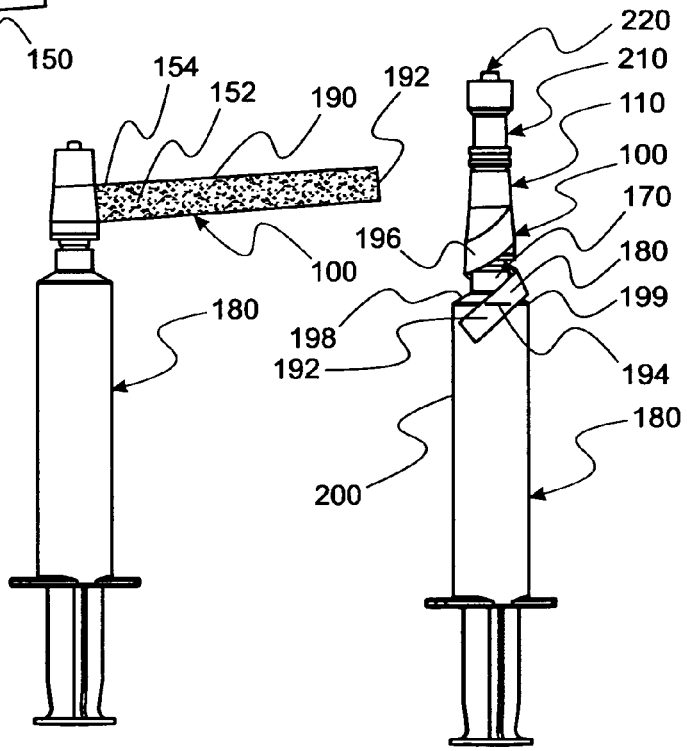
FIG. 5 is a frontal elevation of the combination seen in FIG. 4 with a backing material covering adhesive on the strap removed.
FIG. 6 is a frontal elevation of the combination seen in FIG. 5 with the adhesive strap wound about the dripless connector and adhesively affixed to a barrel of the syringe.

Such a connection is seen in FIG. 4. Once so connected, portion 140 may be digitally grasped to pull backing 150 free from the adhesive face 152 to expose the rest 190 (see FIG. 5) of strap 100. With section 164 wound counter to direction of releasing rotation of threads 130 of luer-lock connection 120, continued winding of the rest 190 of strap 100 and adhesively affixing an end part 192 of strap 100 to the exterior 200 of barrel 180, as seen in FIG. 6, provides a secure cinch for securement of dripless connector 110 to syringe 180.

Note line 194 printed on an exterior side 196 of strap 100. As best adhesion against disengagement is dependent upon the angle strap 100 makes with the barrel edge 198 where barrel is narrowed to communicate with luer-lock fitting 170, affixing end part 192 such that line 194 is parallel to edge 198 assures optimum connector 110 retention by strap 100. As seen in FIG. 6, line 194 is about forty-five degrees offset from edge 199 of strap 100.

The importance of affixing strap 100 to assure solidarity of a luer-lock connection to a syringe barrel is made apparent when considering common modes of using a dripless connector. As seen in FIG. 6, on one end connector 110 is affixed to syringe 180. On the other end, connector 110 is affixed to a needleless connector 210 forming a tandem of two connectors along the same fluid pathway (not shown). Generally, an end 220 of needleless connector 210 away from being connected to dripless connector 110 is securely affixed and is not disengageable.

Another mode of using strip 110 to assure engagement of a dripless connector (e.g. connector 110) to a luer-lock fitting 230 is seen in FIG. 7. In this case a needleless connector 210 is affixed to a "Y" site 240 of an IV set 250. Of course, the connection between fitting 230 and connector 110 is the one for which connection assurance must be provided. Strap 100 is wound about connector 110 and fitting 230 to provide that assurance.

Cross Contamination Barrier

A configuration 310 comprising a syringe barrel 320, a plunger 330, a barrier tube 340 made according to the present invention, and a plunger rod 350, is seen in FIG. 12. At a plunger interfacing end 352, plunger rod 350 comprises a portion 354 which is sized and shaped to be inserted and securely retained within plunger 330 through an insertion orifice 356. Under normal circumstances, plunger rod 350 is simply joined to plunger 330. Commonly, plunger rod 350 comprises a plurality of struts, generally numbered 357. When formed by molding, two of the struts usually have parting lines (not shown in detail) formed as part of molding process. These parting lines often have sharp edges which, when displaced within a syringe barrel can incise material disposed between an edge 357 and an associated inner wall 358 of barrel 320.

Bather tube 340 is seen alone in FIG. 8. At the bottom end 353 bather tube 340 is shaped to conform to the shape of portion 354 (see FIG. 12). A mold or form 360 for making bather tube 340 is seen in FIG. 9. Note that surfaces at top end 362 and bottom end 364 are smooth. However, such is not so for a medial section 366. Between top end 362 and bottom end 364 mold 360 comprises an elongated section 370 disposed below a bulging section 372, the purpose for which is disclosed fully hereafter. Along the surface 374 of sections 370 and 372 is a pattern 374 of grooves, generally numbered 376. While grooves 376 are formed by a spiral pattern, any pattern which provides a raised surface on an inner wall 378 of barrier tube 340 (see FIG. 8) for protecting against a cutting edge (such as an edge of a strut 357, seen in FIG. 12) which may be displaced thereby.

A barrier tube which may be formed by mold 360 is seen in FIGS. 8 and 10. In some cases a plunger similar to plunger 330 but having an orifice through which fluid may be communicated may be used in a multiple chamber syringe. In such cases, a barrier tube 340' may be made to comprise a distal hole, such as hole 380 as seen in FIG. 11. Hole 380 may be formed by molding and then severing an inferiorly disposed nipple subsequent to molding (not shown).

In both barrier tubes, 340 and 340', an open mouth 382 (see FIG. 8) formed by a mold, such as mold 360, is sized and shaped to mechanically seal tightly about barrel 320 (as seen in FIG. 16). Referring again to FIG. 8, the same as for toy balloons, mouth 382 preferably has a rolled edge 384 to tighten and mechanically strengthen an associated seal, as when disposed about barrel 320 (see FIG. 16). Further, barrier tube 340 exhibits an elongated portion 390 and a bulbous portion 391 formed by mold 360 sections 370 and 372, respectively.

Reference is now made to FIGS. 13-16 wherein assembly of barrier tube 340 as a part of assembly of combination 310 is shown. As seen in FIG. 13, plunger rod 350 is inserted into tube 340. If elongated portion 390 comprises a diameter which makes insertion of plunger rod 350 difficult, barrier tube 340 may be slightly inflated to ease insertion. Once plunder rod 350 is fully inserted, barrier tube 340 and plunger rod 350 are affixed to plunger 330 to provide a full plunger assembly 392 as seen in FIG. 14.

The final step in assembly of combination 310 is performed by inserting plunger assembly 392 into barrel 320 as seen in FIGS. 15 and 15A. Commonly, medical syringes have flanges 394 which protrude outward from barrel 320 to provide a digital interface (see FIG. 12). Such an interface should be skid free for proper handling during syringe use. As silicone is commonly used to reduce friction between barrel 320 and plunger 330, an undesirable quantity of silicone may find residence on the exposed surface 396 (see FIG. 16) of a portion of barrier tube 340 when folded about flanges 394 to secure barrier tube 340 (or 340') at a proximal end of barrel 320. Also, dependent upon width and length of flanges 394, bulging portion 391 (see FIGS. 8, 10, 11 and 16) must be enlarged or stretched to accommodate flange 394 size. As stretching has proved to be a source of material failure in barrier tubes without an appropriately sized bulge, form of bulbous portion 391 is deemed a key to a properly formed barrier tube 340. A completed assembly 310, with ribs 398 of bulbous portion 391 exposed for a skid resistant surface is seen in FIG. 15. While applying a lubricant such as silicone to a surface associated with flanges 394 may be undesirable, it has been found that silicone may be advantageously applied at a region of the barrier tube 340 proximal to the insertion area of tube 340 into plunger 330 to reduce deleterious friction threat.

The instant inventions disclosed herein may be embodied in other specific forms without departing from the spirit or essential characteristics thereof. Present embodiments are therefore to be considered in all respects as illustrative and not restrictive, the scope of the inventions being indicated by the appended claims rather than by the foregoing description, and all changes which come within the meaning and range of equivalency of the claims are therefore intended to be embraced therein.

What is claimed to be secured by Letters Patent is:

1. A method for providing a cinch across a first medical friction fit luer-lock connector used in tandem with a second like luer-lock connector whereby likelihood of disengagement of the first luer-lock connector is reduced relative to likelihood of disengagement of the second luer-lock connector to assure a desired disconnection only, said method comprising the steps of:
   (a) providing a first part comprising the first luer-lock connector;
   (b) providing a second part comprising a luer-lock connector which is complimentary to said first luer-lock connector to which the first luer-lock connector is tightly affixed by conventional rotation in a predetermined direction;
   (c) providing an inelastic, elongated planar strap comprising one side having backing material covering an adhesively treated side by which a portion of said backing material is removed to permit said strap to be rotationally affixed to said first part by wrapping said strap rotationally counter to the predetermined direction and by continuing rotation to adhesively affix the strap to the second part;
   (d) using conventional technique, tightly affixing the first part to the second part;
   (e) affixing the strap to the first part by removing backing from a portion of the strap and wrapping that portion of the strap counter to direction of rotation by which the first part is affixed to the second part; and
   (f) removing the remainder of the backing material and continuing wrapping of the strap about the second part and adhesively affixing said strap to said second part whereby strength of engagement is greater than strength of engagement of the second luer-lock connector affixed in tandem with the first luer-lock connector.

2. A method according to claim 1 wherein providing step (a) comprises providing a dripless connector.

3. A method according to claim 2 wherein providing step (b) comprises providing an IV set comprising a luer-lock complimentary fitting whereby the first part is affixed thereto.

4. A method according to claim 2 wherein providing step (b) comprises providing a medical syringe comprising a luer-lock complimentary fitting whereby the first part is affixed thereto.

5. A method according to claim 1 wherein providing step comprises providing a strap comprising adhesively backed material having sufficient tensile strength to withstand conventional pull forces, said strap comprising a 1 mil thick polystyrene material overlaid with a 2 mil thick layer of polyethylene and a permanent high tack adhesive.

6. A method according to claim 5 wherein all of said material is transparent.

7. A method according to claim 1 wherein all parts and material are predetermined to withstand sterilization by radiation.

* * * * *